(12) United States Patent
Chawla et al.

(10) Patent No.: US 10,570,343 B2
(45) Date of Patent: Feb. 25, 2020

(54) SYSTEMS AND METHODS FOR SEPARATING CLASSES OF PARAFFINIC COMPOUNDS

(71) Applicant: ExxonMobil Research and Engineering Company, Annandale, NJ (US)

(72) Inventors: Birbal Chawla, Sterling, VA (US); William G. Borghard, Haddon Heights, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 83 days.

(21) Appl. No.: 15/696,592

(22) Filed: Sep. 6, 2017

(65) Prior Publication Data

US 2018/0079970 A1 Mar. 22, 2018

Related U.S. Application Data

(60) Provisional application No. 62/396,530, filed on Sep. 19, 2016.

(51) Int. Cl.
*C10G 25/03* (2006.01)
*B01J 20/16* (2006.01)
(Continued)

(52) U.S. Cl.
CPC .......... *C10G 25/03* (2013.01); *B01J 20/165* (2013.01); *B01J 29/7007* (2013.01);
(Continued)

(58) Field of Classification Search
None
See application file for complete search history.

(56) References Cited

U.S. PATENT DOCUMENTS 3,054,838 A * 9/1962 Egan ............... C10G 25/03
208/310 R
3,233,003 A 2/1966 Epperly et al.
(Continued)

FOREIGN PATENT DOCUMENTS

EP 0187522 B1 1/1992

OTHER PUBLICATIONS

Hayes, Jr., Paul C. et al., "Paraffins, olefins, naphthenes and aromatics analysis of selected hydrocarbon distillates using on-line column switching high-performance liquid chromatography with dielectric constant detection", Journal of Chromatography, 1988, vol. 437, pp. 365-377.
(Continued)

*Primary Examiner* — Tam M Nguyen
(74) *Attorney, Agent, or Firm* — Glenn T. Barrett

(57) ABSTRACT

Systems and methods for the separation of classes of paraffins from a hydrocarbon sample can include a first column comprising a first zeolite adsorbent material for the isolation of one or more n-paraffins from the hydrocarbon sample and generation of a first eluate including one or more iso-paraffins and one or more one-ring or multi-ring naphthenes. The system can further include a second column, coupled to the first column, comprising a second zeolite adsorbent material for the isolation of one or more iso-paraffins or one-ring naphthenes from the first eluate and generation of a second eluate including one or more multi-ring naphthenes.

10 Claims, 6 Drawing Sheets

(51) Int. Cl.
*B01J 29/70* (2006.01)
*C07C 7/13* (2006.01)
*C07J 9/00* (2006.01)

(52) U.S. Cl.
CPC ............. *B01J 29/7046* (2013.01); *C07C 7/13* (2013.01); *B01D 2253/108* (2013.01); *B01D 2256/24* (2013.01); *C07J 9/00* (2013.01); *C10G 2300/1085* (2013.01)

(56) References Cited

U.S. PATENT DOCUMENTS

| | | | |
|---|---|---|---|
| 4,076,842 A | 2/1978 | Plank et al. | |
| 4,367,364 A * | 1/1983 | Kulprathipanja | C07C 7/13 208/310 R |
| 4,476,713 A | 10/1984 | Alfredson | |
| 4,855,529 A * | 8/1989 | Stem | C07C 5/2791 585/737 |
| 4,956,521 A * | 9/1990 | Volles | C07C 5/2791 585/737 |
| 4,982,052 A | 1/1991 | Nolte | |
| 5,177,299 A * | 1/1993 | McCulloch | C07C 7/13 585/820 |
| 6,022,398 A * | 2/2000 | Cho | B01D 53/053 95/105 |
| 6,069,289 A * | 5/2000 | Dandekar | C07C 7/13 585/734 |
| 6,207,604 B1 | 3/2001 | Yamamoto et al. | |
| 2002/0045793 A1* | 4/2002 | Jolimaitre | C10G 25/03 585/820 |
| 2006/0241330 A1* | 10/2006 | Denayer | B01D 15/00 585/820 |
| 2008/0139863 A1* | 6/2008 | Andersen | C07C 7/13 585/826 |
| 2008/0154084 A1* | 6/2008 | Anderson | B01D 15/00 585/820 |

OTHER PUBLICATIONS

Dutriez, Thomas et al., "Advances in quantitative analysis of heavy petroleum fractions by liquid chromatography—High-temperature comprehensive two-dimensional gas chromotography: Breakthrough for conversion process", Energy & Fuels, 2010, vol. 24, pp. 4430-4438.

Xu, Shiping et al., "An improved method for the micro-separation of straight chain and branched/cyclic alkanes: Urea inclusion paper layer chromatography", Organic Geochemistry, 2005, vol. 36, pp. 1334-1338.

* cited by examiner

SYSTEMS AND METHODS FOR SEPARATING CLASSES OF PARAFFINIC COMPOUNDS

CROSS-REFERENCE TO RELATED APPLICATIONS

This application claims priority to U.S. Provisional Application Ser. No. 62/396,530 filed Sep. 19, 2016, which is herein incorporated by reference in its entirety.

BACKGROUND

Field of the Disclosed Subject Matter

The presently disclosed subject matter relates to a high performance liquid chromatography (HPLC) method for the separation of normal paraffins, iso-paraffins and naphthenes from a hydrocarbon sample.

Description of Related Art

Lubricating base oils, which can be used to formulate engine lubricants and industrial oils, are normally prepared from suitable petroleum feedstocks by a variety of refining processes. These refining processes are generally directed to obtaining lubricating base oils with a predetermined set of properties, for example, viscosity, oxidation stability and maintenance of fluidity over a wide range of temperature. The composition of these lubricating oils can include organic hydrocarbons such as normal paraffins (i.e., n-paraffins), branched paraffins (i.e., iso-paraffins) and cyclic paraffins (i.e., naphthenes). The presence of these paraffinic compounds within the lubricating oil can affect the properties and quality of the lubricating oil. For example, high concentrations of normal paraffins in lubricants can be undesirable, such as raising the pour point of lubricating oil.

Methods for separating and determining the concentration of paraffinic compounds within a hydrocarbon sample are known in the art. For example, U.S. Pat. No. 4,982,052 discloses a process for separating n-paraffins and iso-paraffins from a hydrocarbon sample, which includes the use of two different types of silicalies for selectively adsorbing paraffinic compounds. U.S. Pat. No. 3,233,003 discloses a process for the purification of n-paraffins from a hydrocarbon sample using a silica adsorbent to adsorb n-paraffins from a hydrocarbon sample, and U.S. Pat. No. 4,476,713 discloses a liquid chromatography method for the separation of saturated hydrocarbons from a hydrocarbon sample using micro-particulate materials. Each of these references are hereby incorporated by reference in their entirety. Although these known processes are directed to purifying paraffinic compounds from a hydrocarbon sample, there remains a need for more efficient and more selective processes for separating classes of paraffins in commercial applications.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

The presently disclosed subject matter provides a method of separating classes of paraffinic compounds from a hydrocarbon sample. The method includes providing a hydrocarbon sample and contacting the hydrocarbon sample with a first adsorbent material that includes a zeolite under conditions suitable for the adsorption of one or more n-paraffins to the first adsorbent material and generation of a first eluate that includes one or more iso-paraffins and one or more one-ring or multi-ring naphthenes. The method further includes contacting the first eluate to a second adsorbent material that includes a different zeolite under conditions suitable for the adsorption of one or more iso-paraffins and/or one or more one-ring naphthenes to the second adsorbent material and generation of a second eluate that includes one or more multi-ring naphthenes.

As embodied herein, the zeolite of the first adsorbent material can have a pore size from about 4 Å to about 6 Å. For example, and not by way of limitation, the zeolite of the first adsorbent material can be ZSM-23.

Additionally, the zeolite of the second adsorbent material can have a pore size up to about 7 Å. For example, and not by way of limitation, the zeolite of the second adsorbent material can be Zeolite Beta.

The presently disclosed subject matter further provides a system for the isolation of paraffins from a hydrocarbon sample. The system can include a first column that contains a first zeolite adsorbent material for the isolation of one or more n-paraffins from a hydrocarbon sample and the generation of a first eluate including one or more iso-paraffins and one or more naphthenes, e.g., one-ring and multi-ring naphthenes. The first column may also contain a first solvent containing a mixture that may contain up to about 30% hexane in iso-octane. The system can further include a second column, coupled in fluid communication with the first column that includes a second zeolite adsorbent material for the isolation of one or more iso-paraffins or one-ring naphthenes from the first eluate and the generation of a second eluate including one or more multi-ring naphthenes.

The method can further include desorbing the one or more n-paraffins from the first adsorbent material using a first desorbent to generate a n-paraffin fraction at a temperature up to about 80° C. The first desorbent can include from about 50% hexane in iso-octane to about 100% hexane. As embodied herein, the n-paraffin fraction can include about 80% or more of n-paraffins.

As embodied herein, the method can further include desorbing the one or more iso-paraffins from the second adsorbent material using a second desorbent to generate an iso-paraffin fraction. For example, and not by way of limitation, the second desorbent can include a mixture of solvents containing up to 100% hexane.

Alternatively or additionally, the method can include desorbing the one or more one-ring naphthenes from the second adsorbent material using a third desorbent to generate a one-ring naphthenes fraction at a temperature up to about 100° C. The third desorbent can include a mixture of solvents containing up to 100% hexane.

As embodied herein, the first zeolite adsorbent material can be ZSM-23.

Furthermore, and as embodied herein, the second zeolite adsorbent material can be Zeolite Beta.

It is to be understood that both the foregoing general description and the following detailed description are exemplary and are intended to provide further explanation of the disclosed subject matter claimed.

The accompanying drawings, which are incorporated in and constitute part of this specification, are included to

DETAILED DESCRIPTION OF THE PREFERRED EMBODIMENT

Figure 1:
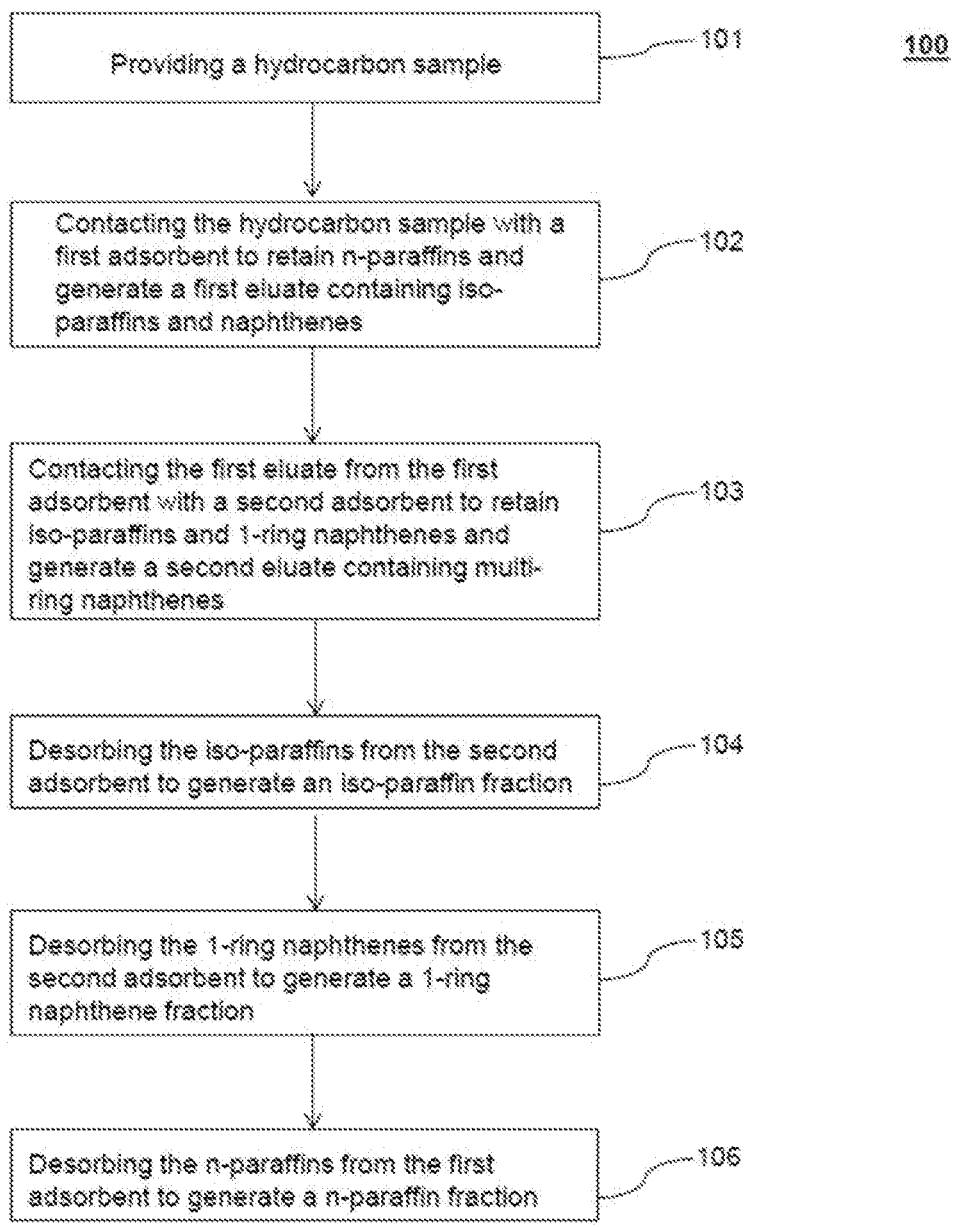
FIG. 1 is a flow chart of an exemplary method for the separation of classes of paraffins from a hydrocarbon sample in accordance with the presently disclosed subject matter.
Figure 2:
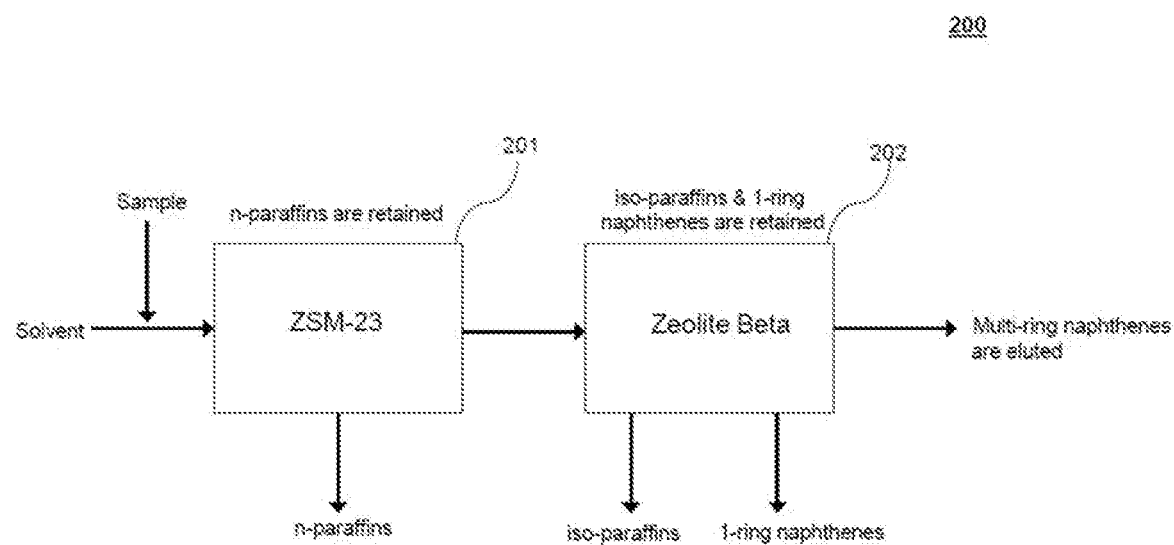
FIG. 2 is a schematic representation of an exemplary system for the separation of classes of paraffins from a hydrocarbon sample in accordance with the presently disclosed subject matter.

Reference will now be made in detail to the various exemplary embodiments of the disclosed subject matter, exemplary embodiments of which are illustrated in the accompanying drawings. The corresponding system of the disclosed subject matter will be described in conjunction with the detailed description of the method.

The systems and methods presented herein can be used for the separation of classes of paraffins from a hydrocarbon sample. The disclosed subject matter is particularly suited for separating n-paraffins, iso-paraffins and naphthenes from hydrocarbon samples, for example, from a lubricating fluid.

In accordance with the disclosed subject matter herein, a method for the separation of classes of paraffinic compounds from a hydrocarbon sample is disclosed. The method includes providing a hydrocarbon sample and contacting the hydrocarbon sample with a first zeolite adsorbent material. Contact between the first adsorbent material and the hydrocarbon sample can be performed under conditions suitable for the adsorption of one or more n-paraffins to the first adsorbent material and the generation of a first eluate including one or more iso-paraffins and one or more one-ring or multi-ring naphthenes. The method can further include contacting the first eluate with a second zeolite adsorbent material under conditions suitable for the adsorption of one or more iso-paraffins or one-ring naphthenes to the second adsorbent material and the generation of a second eluate including one or more multi-ring naphthenes.

In accordance with the disclosed subject matter herein, a system for the separation of classes of paraffinic compounds from a hydrocarbon sample is disclosed. The system includes a first column containing a first zeolite adsorbent material. The first zeolite adsorbent material can adsorb one or more n-paraffins from the hydrocarbon sample and can result in a first eluate including one or more iso-paraffins and one or more one-ring and multi-ring naphthenes. The system can further include a second column, coupled in fluid communication with the first column that contains a second zeolite adsorbent material. The second zeolite material can adsorb one or more iso-paraffins and/or one-ring naphthenes from the first eluate and can result in a second eluate including one or more multi-ring naphthenes.

The accompanying figures, where like reference numerals refer to identical or functionally similar elements throughout the separate views, further illustrate various embodiments and explain various principles and advantages all in accordance with the disclosed subject matter. For purpose of explanation and illustration, and not limitation, exemplary embodiments of methods and systems for separating paraffinic compounds from a hydrocarbon sample in accordance with the disclosed subject matter are shown in FIGS. 1-6. While the present disclosed subject matter is described with respect to using the systems and methods for separating paraffins from a hydrocarbon sample, one skilled in the art will recognize that the disclosed subject matter is not limited to the illustrative embodiment.

FIG. 1 is a flow chart illustrating a representative method implemented according to a non-limiting embodiment of the disclosed subject matter. Referring to FIG. 1, a method for separating paraffins from a hydrocarbon sample 100 includes providing a hydrocarbon sample 101, e.g., a mixture of hydrocarbons. The hydrocarbon samples on which the presently disclosed subject matter can be performed generally include hydrocarbon samples that contain higher paraffins. A "higher paraffin," as used herein, refers to a paraffin with nine or more carbon atoms The hydrocarbon sample can contain hydrocarbons in the lubricant (lube) range. For example, the hydrocarbon sample can include hydrocarbons having equal to or greater than about 15 carbon atoms. Particularly, and not by way of limitation, the hydrocarbon samples can include paraffins having from about 15 to about 40 carbon atoms. The hydrocarbon sample for use in the presently disclosed subject matter can be derived from crude oil and/or petroleum, or other suitable source, e.g. synthetic oils, Fischer-Tropsch oils, shale oils.

As embodied herein, the hydrocarbon sample can include normal paraffins (i.e., n-paraffins), branched paraffins (i.e., iso-paraffins), cyclic paraffins (i.e., naphthenes) or combinations thereof. For example, and not by way of limitation, the hydrocarbon sample can include up to about 95% n-paraffins. Non-limiting examples of n-paraffins that can be present in the hydrocarbon sample can include eicosane ($C_{20}H_{42}$), henicosane ($C_{21}H_{44}$), docosane ($C_{22}H_{46}$), tricosane ($C_{23}H_{48}$), tetracosane ($C_{24}H_{50}$), pentacosane ($C_{25}H_{52}$), triacontane ($C_{30}H_{62}$), dotriacontane ($C_{32}H_{66}$), pentatriacontane ($C_{35}H_{72}$), and tetracontane ($C_{40}H_{82}$). Additionally or alternatively, the hydrocarbon sample can include up to about 95% iso-paraffins. Non-limiting examples of iso-paraffins that can be present in the hydrocarbon sample can include 2-methylhexadecane ($C_{17}H_{36}$), 7-methylhexadecane ($C_{17}H_{36}$), pristane ($C_{19}H_{46}$) and squalane ($C_{36}H_{62}$). Furthermore, the hydrocarbon sample can include up to about 100% naphthenes. Non-limiting examples of naphthenes that can be present in the hydrocarbon sample can include, but are not limited to, n-octadecyl-c-hexane ($C_{24}H_{48}$) and cholestane ($C_{27}H_{48}$).

As noted above and at 102 in FIG. 1, the method of the presently disclosed subject matter 100 further includes contacting the hydrocarbon sample with a first adsorbent to adsorb n-paraffins from the hydrocarbon sample. The hydrocarbon sample can be contacted with a first adsorbent under conditions that adsorb n-paraffins from the hydrocarbon sample to result in a first flow through (i.e., a first eluate) that includes iso-paraffins and naphthenes, e.g., one ring and/or multi-ring naphthenes. For example, and not by way of limitation, the first adsorbent can retain up to about 85% of the n-paraffins initially present in the hydrocarbon sample.

Contacting the hydrocarbon sample with the first adsorbent can be performed using a variety of known techniques. For example, and as embodied herein and depicted in FIG. 2, the hydrocarbon sample can contact a bed of a first adsorbent in a down flow direction (e.g., flow directed by gravity). In non-limiting embodiments, the first adsorbent can be present in a column and the hydrocarbon sample can be applied to a column containing the first adsorbent. As embodied herein, and depicted in 201 of FIG. 2, the bed of a first adsorbent can be contained within a liquid chromatography column. The liquid chromatography column can be, for example, a no-pressure, a low-pressure or a high performance liquid chromatography (HPLC) column. For example, and not by way of limitation, the first adsorbent can be contained within a HPLC column.

As embodied herein, the flow rate of the hydrocarbon sample solution through the first adsorbent can be from about 0.5 ml/min to about 5.0 ml/min, e.g., from about 1.0 ml/min to about 5.0 ml/min, from about 1.0 ml/min to about 4.0 ml/min, from about 1.0 ml/min to about 3.0 ml/min or from about 1.0 ml/min to about 2.0 ml/min. For example, and not by way of limitation, the flow rate of the hydrocarbon sample through the first adsorbent can be about 1.4 ml/min. The temperature at which the hydrocarbon sample contacts the first adsorbent can be from about 20° C. to about 30° C. For example, and not by way of limitation, the temperature can be about 25° C.

As embodied herein, the first adsorbent can include a zeolite adsorbent. Zeolites are classified by the Structure Commission of the International Zeolite Association according to the rules of the IUPAC Commission on Zeolite Nomenclature. A framework-type describes the topology and connectivity of the tetrahedrally-coordinated atoms constituting the framework and makes an abstraction of the specific properties for those materials. Zeolites can possess an internal pore system that includes interconnected cagelike voids or a system of one-, two- or three-dimensional channels. Zeolite adsorbents for which a structure has been established are assigned a three-letter code and are described in the Atlas of Zeolite Framework Types, 5$^{th}$ edition, Elsevier, London, England (2001), which is incorporated in its entirety by reference herein. Zeolites can selectively adsorb molecules based upon differences in molecular size, shape and other properties such as polarity. As embodied herein, the first adsorbent can include a zeolite having a pore diameter from about 4 angstroms (Å) to about 5.5 Å. For example, and not by way of limitation, the first adsorbent can have a pore diameter from about 4.5 Å to about 5.2 Å. Other adsorbents e.g. AlPO's, SAPO's, MeAlO's, SBA-15 can also be used.

As embodied herein, the first adsorbent can be a ZSM-type adsorbent. ZSM (Zeolite Socony Mobil) adsorbents are known in the art and can be commercially obtained or synthesized. Commercially available ZSM-type adsorbents can be obtained from, for example, BASF Corp. (Florham Park, N.J.). For example, and not by way of limitation, the first adsorbent can be selected from ZSM-5, ZSM-11, ZSM-12, ZSM-22, ZSM-23, ZSM-35, ZSM-48, ZSM-50, ZSM-57 or combinations thereof. In non-limiting embodiments, the zeolite can include ZSM-23. The ZSM-23 adsorbent can be used to adsorb n-paraffins, e.g., eicosane from the hydrocarbon sample, to result in a flow through, i.e., a first eluate, that contains iso-paraffins and naphthenes. A non-limiting example of a ZSM-23 adsorbent, including synthesis details, is described in, for example, U.S. Pat. No. 4,076,842, which is hereby incorporated by reference in its entirety. It is contemplated that the zeolites may be extruded (bound) with alumina. It is also contemplated that the zeolite used could be pure or with other inert diluents, but it would need to be formed to a sufficient particle size that permits flow without excessive pressure drop with the first column.

The hydrocarbon sample can contact the first adsorbent material in the presence of a first solvent, e.g., a non-polar solvent. For example, and not by way of limitation, the solvent can contact the first adsorbent prior to and/or after the contact of the hydrocarbon sample with the first adsorbent. Alternatively, the hydrocarbon sample can contact the adsorbent concomitantly with the solvent. The solvent can include one or more lower paraffins. A "lower paraffin," as used herein, includes a paraffin that has one to eight carbon atoms. Non-limiting examples of first solvents for use with the first adsorbent include hexane, iso-hexane, heptane, iso-heptane, octane, iso-octane or combinations thereof. For example, the first solvent can include iso-octane. As embodied herein, the first solvent can include hexane and iso-octane at an amount of about 30% hexane in iso-octane.

As further embodied herein and at 103 of FIG. 1, the method of the presently disclosed subject matter can further include contacting the flow through of the first adsorbent, i.e., first flow through (first eluate), with a second adsorbent. Application of the first flow through to the second adsorbent can be used to adsorb and separate iso-paraffins, e.g., pristane, and one-ring naphthenes from the first flow through, to result in a second flow through (i.e., second eluate) that contains multi-ring naphthenes, e.g., a multi-ring naphthene fraction.

Contacting the flow through from the first adsorbent with the second adsorbent can be performed using a variety of known techniques. For example, and as embodied herein and depicted in FIG. 2, the second adsorbent can be present in a column and the flow through from the first adsorbent can be applied to a column containing the second adsorbent. In non-limiting embodiments, a bed of the second adsorbent can be contained within a liquid chromatography column 202. The liquid chromatography column can be, for example, a no-pressure, a low-pressure or a HPLC column. For example, the second adsorbent can be packed within a HPLC column. Additionally or alternatively, the bed of the first adsorbent can be coupled to the bed of the second adsorbent. For example, and not by way of limitation, the HPLC column containing the first adsorbent can be directly and/or indirectly coupled to the HPLC column containing the second adsorbent. The column containing the second adsorbent can be in fluid communication with the column containing the first adsorbent.

As embodied herein, the flow rate of the flow through the second adsorbent can be from about 0.5 ml/minute to about 5.0 ml/minute. The temperature at which the first flow through contacts the second adsorbent can be from about 10° C. to about 80° C. For example, and not by way of limitation, the temperature can be about 25° C. Furthermore, the temperature can be about 50° C.

In non-limiting embodiments, the second adsorbent can include a zeolite adsorbent. For example, and not by way of limitation, the second adsorbent can include a zeolite having a pore diameter from about 4 Å to about 7 Å. Additional types of adsorbents that can be used are aluminosilicates, aluminophosphates, metallophosphates, mesoporous aluminosilicates, microporous carbons, MOF's (metal organic frameworks), and ZIF's (zeolitic imidazolate frameworks). For example, and not by way of limitation, the second adsorbent can be selected from ZSM-5, ZSM-11, ZSM-12, ZSM-22, ZSM-35, ZSM-48, ZSM-50, ZSM-57, Zeolite Beta, Zeolite Y, Zeolite omega, EU-1, NU-87, Zeolite L, MCM-22, SSZ-25, MCM-36, MCM-49, MCM-56, MCM-58 or combinations thereof e.g. hierarchical materials. As embodied herein, the zeolite of the second adsorbent can include Zeolite Beta. The Zeolite Beta adsorbent can be used to adsorb iso-paraffins, e.g., 7-methylhexadecane, and one-ring naphthenes, e.g., n-octadecyl-cyclo-hexane, from the first flow through, to result in a second flow through that contains multi-ring naphthenes. Zeolite Beta adsorbents, including synthesis details, are described in, for example, EP Patent Application No. EP0187522 and U.S. Pat. No. 6,207,604. Each of these references are hereby incorporated by reference in their entirety. As embodied herein, the zeolite Beta was used after extruding it with an alumina binder.

The first flow through can contact the second adsorbent material in the presence of a second solvent. For example, and not by way of limitation, the solvent can include one or more lower paraffins, as described above. The second solvent can include hexane, iso-hexane, heptane, iso-heptane, octane, iso-octane or combinations thereof. As embodied herein, the second solvent can include hexane. Additionally or alternatively, the second solvent can include iso-octane. For example, the second solvent can include a mixture containing about 30% hexane in iso-octane.

In accordance with another aspect of the disclosed subject matter, the method disclosed herein can further include the release of the adsorbed hydrocarbons from the adsorbents to generate purified fractions of n-paraffins, iso-paraffins and one-ring naphthenes. The method, therefore, can further include desorbing iso-paraffins from the second adsorbent 104. For example, and not by way of limitation, the method can include contacting the second adsorbent with a second desorbent to generate an iso-paraffin fraction. As embodied herein, the iso-paraffin fraction generated by the disclosed method can have a purity greater than about 90%.

Figure 3:
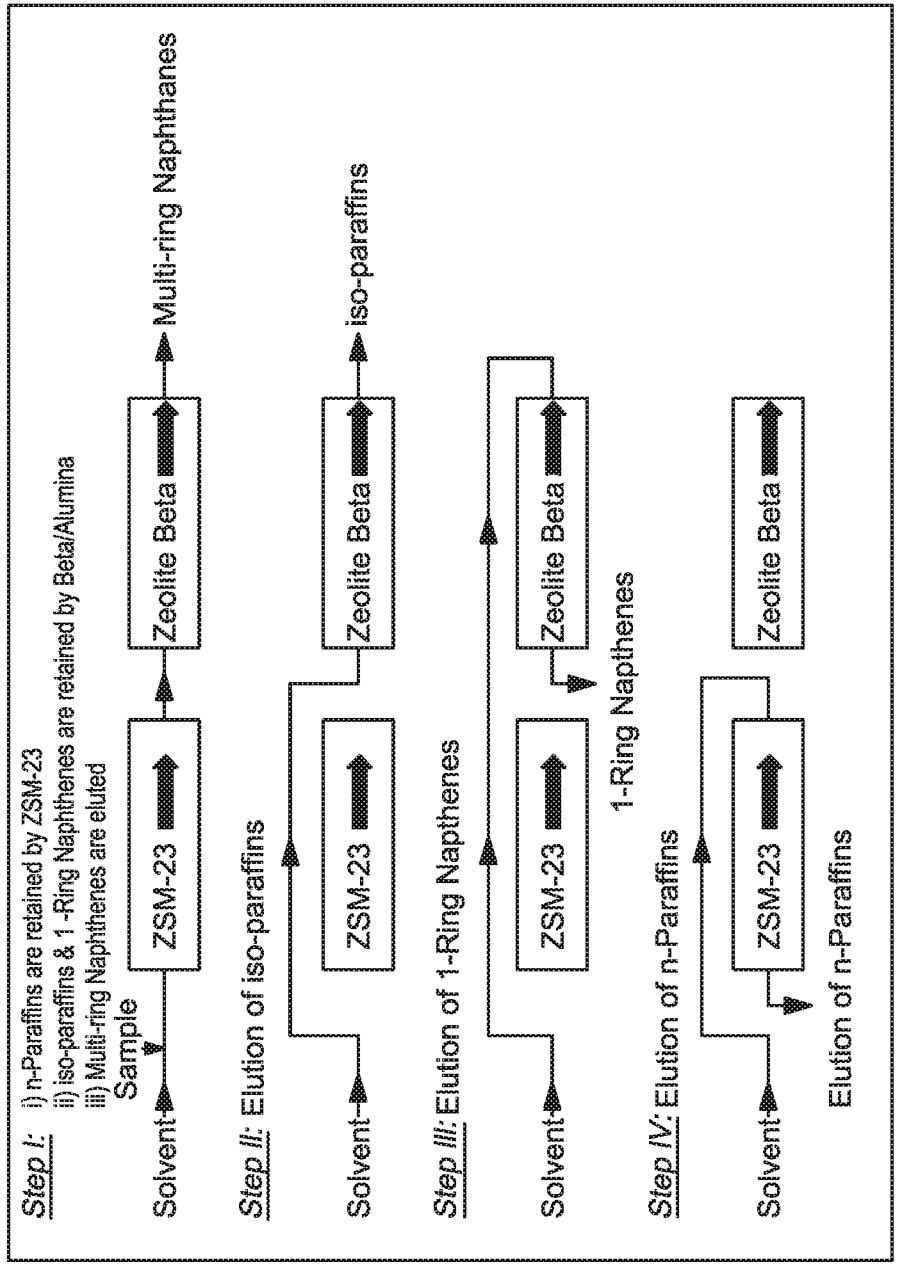
FIG. 3 is a schematic representation of an exemplary method for the separation of classes of paraffins from a hydrocarbon sample in accordance with the presently disclosed subject matter.

As embodied herein and depicted in FIG. 3, desorption of the iso-paraffins can include forward-flushing the second adsorbent with a second desorbent. The second desorbent can include preferably 100% hexane, but it is contemplated that the second desorbent can be a mixture of solvents containing up to 100% hexane. Additionally, the desorption of the iso-paraffins can occur within at least 15 minutes after application of the first flow through to the second adsorbent and/or can occur at a temperature from about 15° C. to about 25° C.

As embodied herein and depicted at 105 in FIG. 1, the method can further include desorbing 1-ring naphthenes from the second adsorbent. For example, and not by way of limitation, the method can include contacting the second adsorbent with a third desorbent to generate a one-ring naphthene fraction 105.

As embodied herein and depicted in FIG. 3, desorption of the one-ring naphthenes can include back-flushing (e.g., reverse flushing) the second adsorbent with a third desorbent. The third desorbent can include preferably 100% hexane, but it is contemplated that the third desorbent can be a mixture of solvents containing up to 100% hexane. Additionally, the desorption of one-ring naphthenes can occur within at least 15 minutes after application of the first flow through to the second adsorbent and/or can occur at a temperature from about 80° C. to about 100° C.

As embodied herein and depicted at 106 in FIG. 1, the method can further include desorbing the n-paraffins from the first adsorbent to generate a n-paraffin fraction. The n-paraffin fraction generated by the disclosed method can have purity greater than about 75%, greater than about 80%, greater than about 85%, greater than about 90% or greater than about 95%. For example, and not by way of limitation, the n-paraffin fraction can have purity from about 80% to about 85%.

As embodied herein and depicted in FIG. 3, desorption of the n-paraffins can include back-flushing the first adsorbent with a first desorbent. The first desorbent can include a lower paraffin, as described above, such as, but not limited to, hexane. For example, and not by way of limitation, the first desorbent can include about 50% hexane in iso-octane to about 100% hexane. The desorption of n-paraffins from the first adsorbent can occur within at least 15 minutes after application of the hydrocarbon sample to the first adsorbent and/or can occur at a temperature from about 80° C. or above.

Desorption of the iso-paraffins, n-paraffins and one-ring naphthenes from the adsorbents can occur in any order. For example, and not by way of limitation, desorption of the n-paraffins from the first adsorbent can occur prior to the desorption of the iso-paraffins and/or naphthenes from the second adsorbent.

The zeolite adsorbents used in the presently disclosed subject matter can be used in any form. For example, and not by way of limitation, a zeolite can be used in the form of beaded particles, crushed particles or extruded particles. The zeolite can be used alone, or in association with known binders including, but not limited to, silica, alumina, aluminosilicates, titania, zirconia, or clays such as kaolin and attapulgite. In accordance with another aspect of the disclosed subject matter, the methods disclosed herein can further include analyzing and quantifying the purified fractions. For example, and not by way of limitation, the fractions generated by the disclosed method can be further analyzed by gas chromatography, gas chromatography-mass spectrometry, nuclear magnetic resonance and/or 2D-gas chromatography for quantification of the n-paraffins, iso-paraffins, one-ring and multi-ring naphthenes that were present in the hydrocarbon sample.

Example 1: Evaluation of Zeolite Adsorbents

The presently disclosed subject matter is illustrated in greater detail by the specific Example presented below and as depicted in FIG. 3. It is understood that this Example is an illustrative embodiment and is not intended to be limiting in any way.

Several zeolites with varying pore diameters were evaluated for HPLC separation of n-paraffins, iso-paraffins and naphthenes within the lube range from a hydrocarbon sample. As these three classes of compounds have very similar adsorption characteristics, the compounds cannot be separated using HPLC columns packed with routinely used adsorbents. However, the three classes of compounds have different kinetic sizes/shapes, and therefore could be separated using different adsorbents having different pores. The zeolites that were tested are listed below in Table 1.

TABLE 1

Zeolites Used as Adsorbents

| Zeolite | Pore Diameter | HPLC Behavior |
|---|---|---|
| ZSM-23 | 4.5-5.2 Å | Found suitable for retaining normal paraffins |
| ZSM-48 | 5.3-5.6 Å | Found un-suitable (partial retention of iso-paraffins) |
| ZSM-12 | 5.3-6.0 Å | Found un-suitable (partial retention of iso-paraffins) |
| ZSM-5 | Dual Channels: 5.1-5.5 Å & 5.3-5.6 Å | Found un-suitable (partial retention of iso-paraffins) |
| Zeolite Beta | Three Channels: Up to 7.0 Å | Found suitable for separating iso-paraffins from naphthenes |

In this Example, the hydrocarbon sample used was a total saturates fraction obtained using in-house liquid chromatographic separation of a gas oil blend with a boiling range of 563-1029° F. The hydrocarbon sample was applied to a 10 mm×10 mm HPLC column packed with the ZSM-23 adsorbent at a flow rate of 1.4 ml/min in the presence of a solvent (e.g., iso-octane or 30% hexane in iso-octane; see Table 2). The hydrocarbon sample was applied to the ZSM-23 column at a temperature of 25° C. to adsorb the n-paraffins from the hydrocarbon sample and generate a flow through that contains iso-paraffins and cyclic paraffins (1-ring and multi-ring naphthenes). The n-paraffins adsorbed to the ZSM-23 column were desorbed from the column by back-flushing at 80° C. with 50-100% hexane (see FIG. 3).

The effluent from the ZSM-23 column was subsequently applied to a column packed with Zeolite Beta adsorbent at a temperature of 15° C. or 25° C. The flow through of the ZSM-23 column was applied to the Zeolite Beta column in the presence of a solvent (e.g., iso-octane or 30% hexane in iso-octane) to adsorb branched paraffins and 1-ring naphthenes to generate a flow through that contains multi-ring naphthenes. The branched paraffins and one-ring naphthenes were subsequently desorbed from the Zeolite Beta adsorbent (see FIG. 3) using 100% hexane in forward and reverse solvent flow modes at 25° C. and 80° C., respectively. Mixtures of solvents containing hexane are contemplated to be within the scope of the present invention.

After evaluating 5 zeolites of varying pore sizes, two adsorbents were identified to be suitable for separating n-paraffins from iso-paraffins and naphthenes, and for separating iso-paraffins and one-ring naphthenes from multi-ring naphthenes. These adsorbents are ZSM-23 and Zeolite Beta. ZSM-23 was found to be very selective for retaining and separating n-paraffins from rest of the saturated hydrocarbons within the sample. The adsorption characteristics of ZSM-23 and Zeolite Beta were explored using various n-paraffinic, iso-paraffinic and naphthenic model compounds (see Table 2).

TABLE 2

HPLC Behaviors of Selected Model Compounds

| | HPLC Elution | | | | | |
|---|---|---|---|---|---|---|
| | ZSM-23 | | Zeolite Beta | | | |
| Compound Description/Eluting Solvent | Iso-octane | 30% n-hexane in Iso-octane | Iso-octane | 30% n-hexane in Iso-octane | Hexane | Hexane (different temperatures) |
| n-Eicosane, $C_{20}H_{42}$ (normal alkane) | Retained | Retained | Retained | Retained | Eluted (late) | |
| n-Dotriancontane, $C_{32}H_{66}$ (normal alkane) | Retained | Retained | | | Retained | |
| 2-Methylhexadecane, $C_{17}H_{36}$ (mono-methyl alkane) | Retained | Eluted | Retained | Retained | Eluted (Partially) | Eluted (Broad) at 50° C. |
| 7-Methylhexadecane, C17H36 (mono-methyl alkane) | Retained | Eluted | Retained | Retained (Partially) - 20% & 30% hexane in iso-octane | Eluted (Broad) | Eluted (Broad) at 50° C. Eluted at 15° C. |
| Pristane, $C_{19}H_{40}$ (branched alkane) | Eluted | Eluted | Retained | Retained | Eluted | |
| Squalane, $C_{30}H_{62}$ (branched alkane) | Eluted | Eluted | Retained | Retained | Eluted | |
| n-Octadecyl-c-hexane, $C_{24}H_{48}$ (1-ring naphthene) | Retained | Eluted | Retained | Retained | Retained | Retained at 50° C. |
| Cholestane, $C_{27}H_{48}$ (multi-ring naphthenic alkane) | Eluted | Eluted | Eluted | Eluted | Eluted | |

Figure 4:
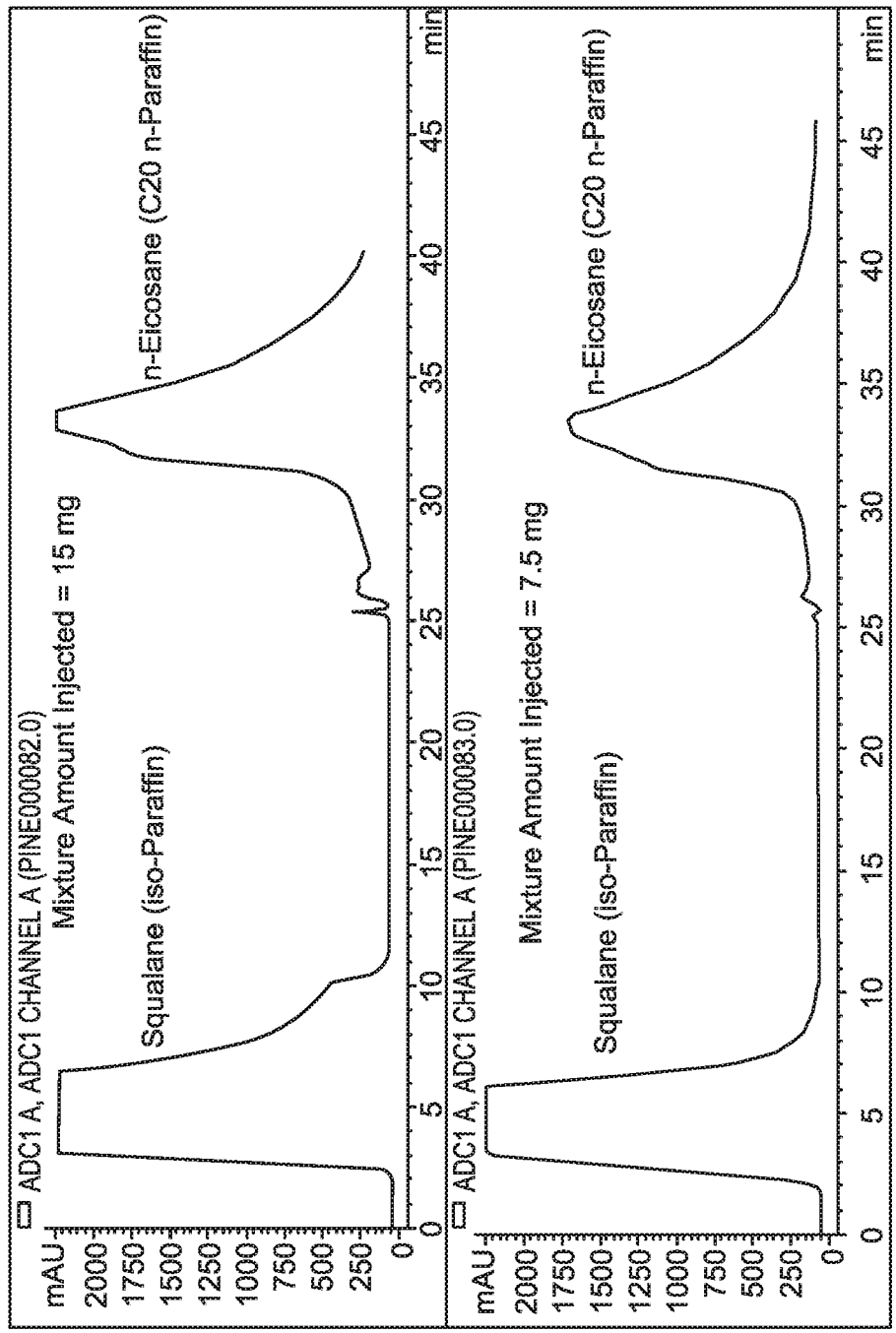
FIG. 4 depicts the resulting HPLC separation chromatograms for n-eicosane and squalane from Example 1 using a method in accordance with a non-limiting embodiment of the presently disclosed subject matter.
Figure 5:
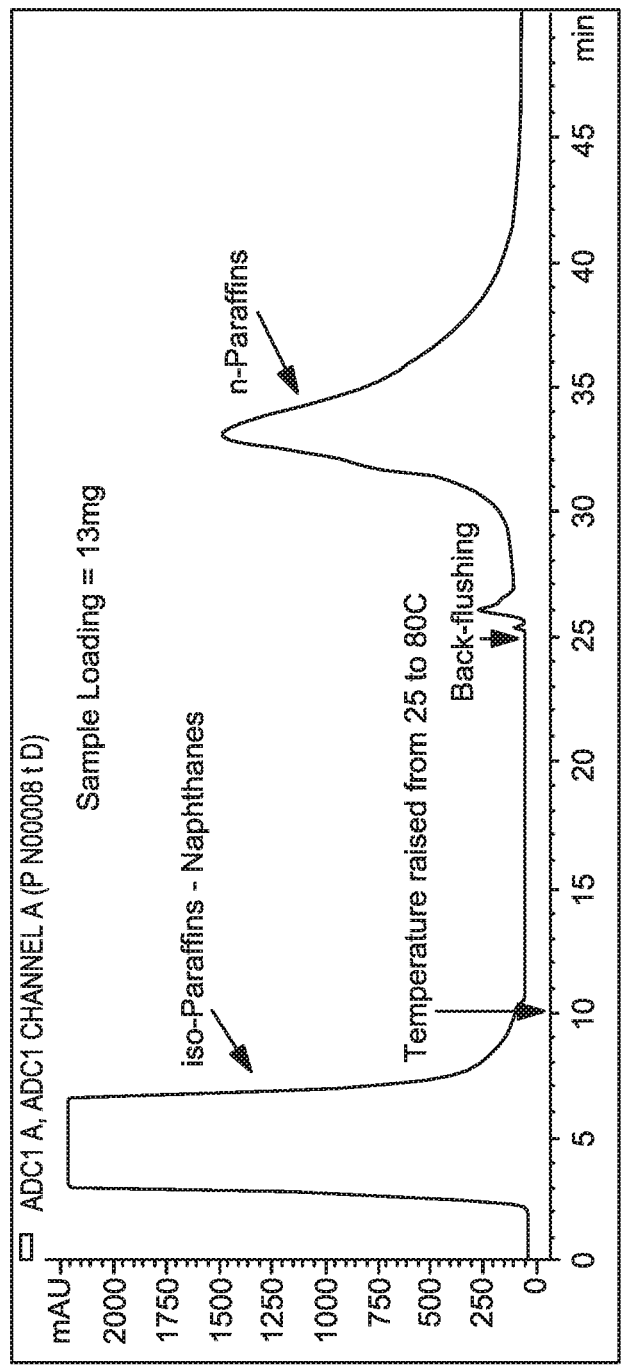
FIG. 5 depicts the resulting HPLC separation chromatogram for total saturates of a gas oil blend from Example 1 using a method in accordance with a non-limiting embodiment of the presently disclosed subject matter.
Figure 6:
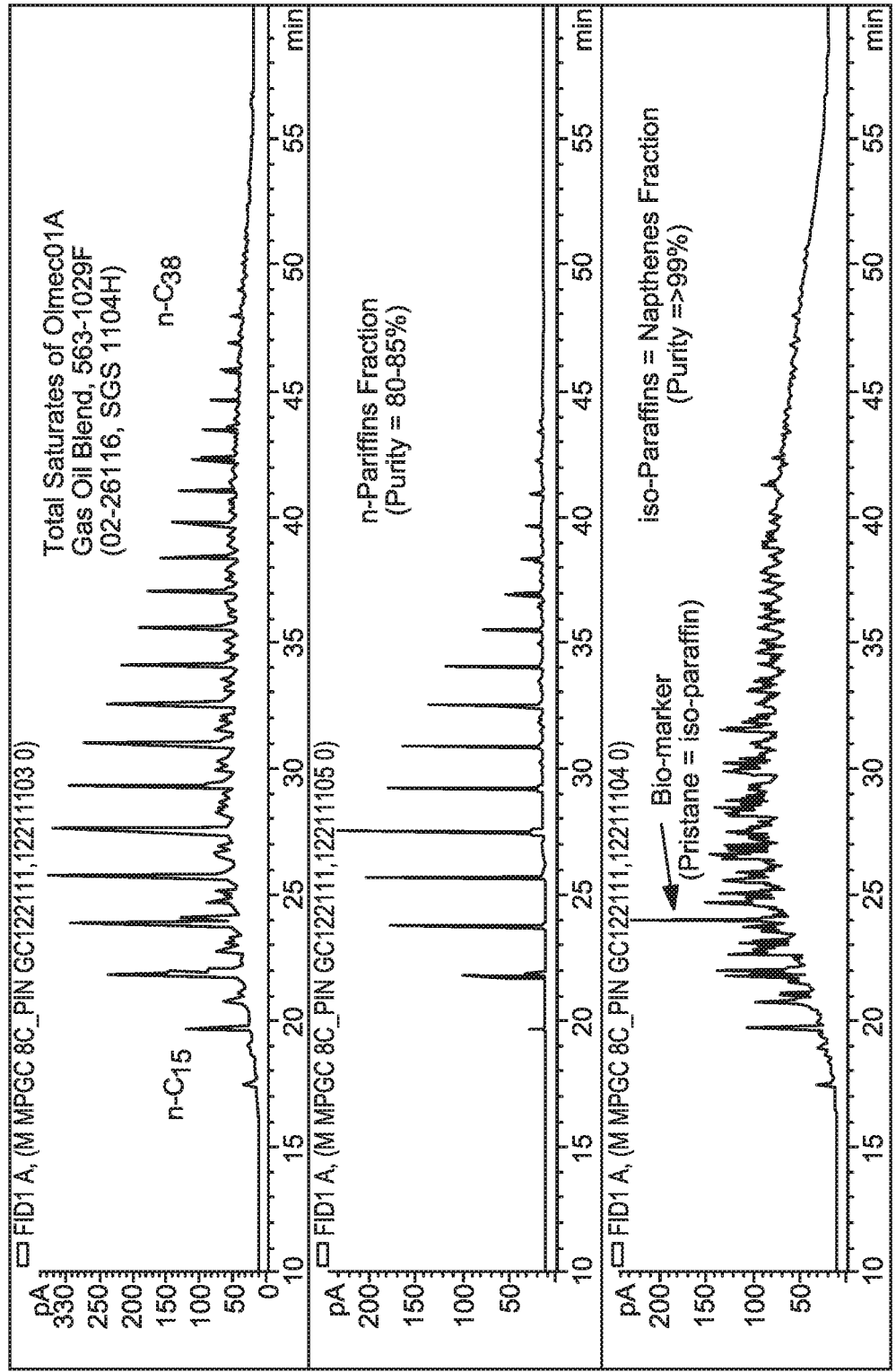
FIG. 6 depicts the resulting gas chromatography-flame ionization detector (FID) chromatograms of HPLC separated fractions along with total saturated hydrocarbons from Example 1.

In order to determine the loading capacity of the adsorbent (ZSM-23), a mixture of n-eicosane ($C_{20}H_{42}$ n-paraffin) and squalane (multi-methyl iso-paraffin) were separated. HPLC separation chromatograms for these two compounds are shown in FIG. 4. As shown in the HPLC chromatograms, the ZSM-23 efficiently adsorbed the n-paraffin eicosane resulting in a flow through (i.e., eluate) that contains the iso-paraffin squalane (FIG. 4). Once loading amount was established, a total saturates sample was separated. The separation chromatogram, along with the HPLC conditions for the separation of total saturates of a gas oil blend with ZSM-23, are shown in FIG. 5. As shown in FIG. 5, ZSM-23 retained the n-paraffins resulting in a flow through (i.e., eluate) that contained iso-paraffins and naphthenes when performed at a temperature of 25° C. in the presence of the 30% hexane in iso-octane solvent. To desorb the n-paraffins from the ZSM-23 adsorbent, the temperature was raised to 80° C. and back-flushed using a solvent that includes 50-100% hexane.

The HPLC separation results along with a Vendor data (a limited data set) are shown below in Table 3 for comparison purposes. The quality of the separated fractions was checked by gas chromatography (GC) using a flame ionization detector (FID). The recovery data (shown in Table 3) along with the GC chromatograms shown in FIG. 6 clearly establish the superiority of the separation.

TABLE 3

HPLC Separation Results

| | PIN Analysis | Vendor Data |
|---|---|---|
| Sample Loading (mg) | 13 | 40 |
| Recovery (wt %) | 92.2 | 37 |
| n-Paraffins (% norm; excluding solvent) | 21.7 | |
| iso-Paraffins + naphthenes (% norm; excluding solvent) | 78.3 | |
| Purity of n-paraffins (GC analysis) | 80-85% | 48% |
| Purity of iso-paraffins + naphthenes fraction (GC analysis) | >99% | >95% |

As disclosed above, a HPLC method has been successfully developed and used to isolate n-paraffins from rest of the lube range saturated hydrocarbons, and for the separation of iso-paraffins and one-ring naphthenes from multi-ring naphthenes. A complete separation scheme is depicted in FIG. 3, which allows the separation of classes of paraffinic compounds from a hydrocarbon sample for characterization of the composition of the hydrocarbon sample.

Accurate detail compositional characterization of paraffinic and naphthenic structures present in lube-range materials is very valuable in obtaining cold flow property predictions and property models (pour, viscosity, etc.) to allow the determination of the value of the lube materials. In addition, the isolation of pure fractions will be highly useful for optimizing advanced characterization analytical techniques such as GC, GC-MS, NMR and 2DGC, which are used for heavy petroleum streams. Such information can be used to adjust and enhance operating parameters in refinery and petroleum operations. Such information will also be highly useful in selecting lube basestocks for blending high quality lubes.

Additional Embodiments

Additionally or alternatively, the invention can include one or more of the following embodiments.

Embodiment 1

A method of isolating classes of paraffins from a hydrocarbon sample, comprising: (a) providing a hydrocarbon sample; (b) contacting the hydrocarbon sample with a first Zeolite adsorbent material comprising a zeolite under conditions suitable for adsorption of one or more n-paraffins to the first adsorbent material and generation of a first eluate comprising one or more iso-paraffins and one or more one-ring or multi-ring naphthenes; and (c) contacting the first eluate with a second adsorbent material comprising a zeolite under conditions suitable for adsorption of one or more iso-paraffins or one-ring naphthenes to the second adsorbent material and generation of a second eluate comprising one or more multi-ring naphthenes.

Embodiment 2

The method of embodiment 1, wherein the zeolite of the first adsorbent material has a pore size from about 4 Å to about 6 Å.

Embodiment 3

The method of embodiment 1 or 2, wherein the zeolite of the first adsorbent material is ZSM-23.

Embodiment 4

The method of any of the preceding embodiments, wherein the zeolite of the second adsorbent material has a pore size up to about 7 Å.

Embodiment 5

The method of any of the preceding embodiments, wherein the zeolite of the second adsorbent material is Zeolite Beta.

Embodiment 6

The method of any of the preceding embodiments, further comprising desorbing the one or more n-paraffins from the first adsorbent material using a first desorbent to generate a n-paraffin fraction.

Embodiment 7

The method of embodiment 6, wherein the first desorbent comprises from about 50% hexane in iso-octane to about 100% hexane.

Embodiment 8

The method of embodiment 6, wherein the n-paraffin fraction comprises about 80% or more of paraffins.

Embodiment 9

The method of any of the preceding embodiments, further comprising desorbing the one or more iso-paraffins from the second adsorbent material using a second desorbent to generate an iso-paraffin fraction.

Embodiment 10

The method of embodiment 9, wherein the second desorbent comprises a mixture containing up to 100% hexane.

Embodiment 11

The method of any of the preceding embodiments, further comprising desorbing the one or more one-ring naphthenes from the second adsorbent material using a third desorbent to generate a one-ring naphthene fraction.

Embodiment 12

The method of embodiment 1, wherein the third desorbent comprises a mixture of solvents containing up to 100% hexane.

Embodiment 13

The method according to any of the preceding embodiments, wherein contacting the hydrocarbon sample with a first Zeolite adsorbent material further includes contacting the hydrocarbon sample with a first solvent containing about 30% hexane in iso-octane.

Embodiment 14

A method of isolating classes of paraffins from a hydrocarbon sample, comprising: (a) providing a hydrocarbon sample; (b) contacting the hydrocarbon sample with a first adsorbent material comprising a zeolite under conditions suitable for adsorption of one or more n-paraffins to the first adsorbent material and generation of a first eluate comprising one or more iso-paraffins and one or more one-ring or multi-ring naphthenes; (c) contacting the first eluate with a second adsorbent material comprising a zeolite under conditions suitable for adsorption of one or more iso-paraffins or one-ring naphthenes to the second adsorbent material and generation of a second eluate comprising one or more multi-ring naphthenes; (d) desorbing the one or more iso-paraffins from the second adsorbent material using a second desorbent to generate an iso-paraffin fraction; (e) desorbing the one or more one-ring naphthenes from the second adsorbent material using a third desorbent to generate a one-ring naphthene fraction; and (f) desorbing the one or more n-paraffins from the first adsorbent material using a first desorbent to generate a n-paraffin fraction.

Embodiment 15

A system for the isolation of classes of paraffins from a hydrocarbon sample, comprising: (a) a first column comprising a first zeolite adsorbent material for isolation of one or more n-paraffins from the hydrocarbon sample and generation of a first eluate comprising one or more iso-paraffins and one or more one-ring or multi-ring naphthenes; and (b) a second column, coupled in fluid communication with the first column, comprising a second zeolite adsorbent material for isolation of one or more iso-paraffins or one-ring naphthenes from the first eluate and generation of a second eluate comprising one or more multi-ring naphthenes.

Embodiment 16

The system of embodiment 15, wherein the first zeolite adsorbent material has a pore size from about 4 Å to about 6 Å.

Embodiment 17

The system of embodiments 15 or 16, wherein the first zeolite adsorbent material is ZSM-23.

Embodiment 18

The system of any one of embodiments 15-17, wherein the second zeolite adsorbent material has a pore size up to about 7 Å.

Embodiment 19

The system of any one of embodiments 15-17, wherein the second zeolite adsorbent material is Zeolite Beta.

While the disclosed subject matter is described herein in terms of certain preferred embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method of isolating classes of paraffins from a hydrocarbon sample, comprising:
   (a) providing a hydrocarbon sample;
   (b) contacting the hydrocarbon sample with a first adsorbent material comprising a zeolite under conditions suitable for adsorption of one or more n-paraffins to the first adsorbent material and generation of a first eluate comprising one or more iso-paraffins and one or more one-ring or multi-ring naphthenes;
   (c) contacting the first eluate with a second adsorbent material comprising a zeolite under conditions suitable for adsorption of one or more iso-paraffins or one-ring naphthenes to the second adsorbent material and generation of a second eluate comprising one or more multi-ring naphthenes;
   (d) desorbing the one or more iso-paraffins from the second adsorbent material using a second desorbent to generate an iso-paraffin fraction;
   (e) desorbing the one or more one-ring naphthenes from the second adsorbent material using a third desorbent to generate a one-ring naphthene fraction; and
   (f) desorbing the one or more n-paraffins from the first adsorbent material using a first desorbent to generate a n-paraffin fraction.

2. The method of claim 1, wherein the zeolite of the first adsorbent material has a pore size from about 4 Å to about 6 Å.

3. The method of claim 1, wherein the zeolite of the first adsorbent material is ZSM-23.

4. The method of claim 1, wherein the zeolite of the second adsorbent material has a pore size up to about 7 Å.

5. The method of claim 1, wherein the zeolite of the second adsorbent material is Zeolite Beta.

6. The method of claim 1, wherein the first desorbent comprises from about 50% to about 100% hexane.

7. The method of claim 1, wherein the n-paraffin fraction comprises about 80% or more of paraffins.

8. The method of claim 1, wherein the second desorbent comprises a mixture of solvents containing up to 100% hexane.

9. The method of claim 1, wherein the third desorbent comprises a mixture of solvents containing up to 100% hexane.

10. The method according to claim 1, wherein contacting the hydrocarbon sample with a first Zeolite adsorbent material further includes contacting the hydrocarbon sample with a first solvent containing about 30% hexane in iso-octane.

* * * * *